United States Patent
Itsygin

(12)
(10) Patent No.: US 6,322,680 B1
(45) Date of Patent: Nov. 27, 2001

(54) UNIVERSAL ION-SELECTIVE METER

(75) Inventor: Semen Borisovich Itsygin, Moskovskaya obl. (RU)

(73) Assignee: Advanced Biosensors, San Diego, CA (US)

( * ) Notice: Subject to any disclaimer, the term of this patent is extended or adjusted under 35 U.S.C. 154(b) by 0 days.

(21) Appl. No.: 08/849,251

(22) PCT Filed: Dec. 14, 1995

(86) PCT No.: PCT/RU95/00272

§ 371 Date: Sep. 30, 1997

§ 102(e) Date: Sep. 30, 1997

(87) PCT Pub. No.: WO96/18889

PCT Pub. Date: Jun. 20, 1996

(30) Foreign Application Priority Data

Dec. 15, 1994 (RU) .................................................. 94043082

(51) Int. Cl.⁷ ....................... G01N 27/401; G01N 27/403
(52) U.S. Cl. ........................ 204/416; 204/420; 204/422; 204/435
(58) Field of Search .................... 204/435, 420, 204/416, 422

(56) References Cited

U.S. PATENT DOCUMENTS

| | | | |
|---|---|---|---|
| 3,652,439 | * | 3/1972 | Ben-Yaakov et al. ............... 204/420 |
| 3,997,420 | * | 12/1976 | Buzza .................................. 204/420 |
| 4,018,661 | * | 4/1977 | Brushwyler et al. ............... 204/420 |
| 4,154,660 | * | 5/1979 | Micko ................................. 204/420 |
| 4,279,728 | * | 7/1981 | Horii ................................... 204/400 |
| 4,632,732 | * | 12/1986 | Fog et al. ............................ 204/420 |
| 4,959,138 | * | 9/1990 | Brinkmann et al. ................ 204/435 |

(List continued on next page.)

FOREIGN PATENT DOCUMENTS

| | | |
|---|---|---|
| 0043653 | 1/1982 | (EP) . |
| 0 095 376 | 11/1983 | (EP) . |
| 0115884 | 8/1984 | (EP) . |
| 1 452 402 | 10/1976 | (GB) . |
| 298882 | 3/1971 | (SU) . |
| WO 88/00700 | 1/1988 | (WO) . |

OTHER PUBLICATIONS

Biochemical Preparations Inc., Immersion Flow Recorder — For Measuring pH in sterile media, Derwent abstract for Soviet Union Patent # 344,848, May 1971.*
SU Abstract 296882A Jul. 1972.
Abstract of German Published Patent Application 3,100,302 A Based on Austrian Application 363062 B. Oct. 1981.
Product Specifications; 871PH Series pH, ORP, and Fluoride Sensors and Accessories, pp. 1–15, Foxboro Company Catalog (1990–1995) month N/A.

(List continued on next page.)

Primary Examiner—Robert J. Warden, Sr.
Assistant Examiner—Kaj K. Olsen
(74) Attorney, Agent, or Firm—Foley & Lardner

(57) ABSTRACT

The proposed multipurpose ion-selective sensor is designed to be operational in any spatial position in harsh environment and incorporates a housing tube (1) where a number of elements are fixed and electrically connected to a measurement transmitter; these members include: a detachable indicator electrode (3) which employs a solid indicator system (33) with a solid membrane contacting the analysed liquid; a detachable reference electrode (4) with a hollow body (20) accommodates a potential-forming semi-element (21), a connecting member (22) and electrolyte (29) filled with a solid dispersed material forming a spatial structure (30) in the electrolyte (29), whereby the structure is rigidly linked with internal surface (31) of the reference electrode (4) body (20), the potential-forming semi-element (21) and with the connecting member (22).

9 Claims, 4 Drawing Sheets

U.S. PATENT DOCUMENTS

| | | | |
|---|---|---|---|
| 5,071,537 | * 12/1991 | Yamaguchi et al. | 204/435 |
| 5,139,641 | * 8/1992 | Neukum | 204/435 |
| 5,360,529 | * 11/1994 | Edwards et al. | 204/435 |
| 5,417,836 | * 5/1995 | Masuda et al. | 204/416 |
| 5,830,338 | * 11/1998 | Seto et al. | 204/416 |

OTHER PUBLICATIONS

Ingold Catalog; PH/Redox Measurement In Chemical Processes, pp. 1–20 date N/A.

Ingold AG; "Practice and Theory of pH Measurement", pp. 4–87, (1989) month N/A.

Orion Research Incorporated, "Ion–Selective Electrode Catalog and Guide to Ion Analysis", pp. 1–3, (1992) month N/A.

Ingold Catalog; "pH/Redox Measurement in Biotechnology", p. 10 date N/A.

Broadley James Corporation; "Cutaway Views of the pH Fermprobe Double Junction Reference System" date N/A.

Ingold Catalog; "Your Guide to Laboratory Electrodes", pp. 1–8 date N/A.

Jumo Mess—Und Regeltechnik Catalog; "Elektroden für ph, Redox, Leitfähigkeit im Labor und Betrieb" date N/A.

Inlab Standard Electrodes Catalog; "Reliability and Precision for Professionals", pp. 7–10 date N/A.

* cited by examiner

UNIVERSAL ION-SELECTIVE METER

APPLICATION AREA

The invention relates to devices for ion composition and redox potential monitoring in process fluids, natural water and sewage, and specifically, a multipurpose ion-selective sensor.

BACKGROUND OF THE INVENTION

Numerous ion-selective sensors designed for monitoring of hydrogen ions in various process fluids are widely known.

Such examples include, in particular, a ion-selective sensor described by P. Meier, A. Lohrum and J. Gareess (Editors) in the study, "Practice and Theory of pH Measurement", Ingold Messtechnik A G, CH-B902 Undorf/Switzerland, 1989, p. 15. This combined sensor comprises a glass tube body incorporating glass indicator and reference electrodes filled with a liquid electrolyte.

Another known ion-selective sensor (a Switzerland's Ingold booklet "pH/Redox Measurement in Biotechnology. pH-Electrodes. Industrial Probes. Sensors," Ingold Messtechnik A G, CH-8902 Urdorf/Switzerland 1990, p. 10) has a similar design, but its reference electrode is filled with a gel-type electrolyte.

The both above mentioned sensors have a monolithic glass design and require refillings of their reference electrodes. These sensors are only suitable for predefined spatial positions and are inoperable in harsh conditions (elevated temperatures and those below 0° C., high pressures, zero-gravity and other conditions). Sensors intended for redox potential monitoring are widely employed at present. For instance, a sensor with a reference electrode filled with gel electrolyte and an indicator electrode with a platinum or gold sensing element have been described in a booklet titled "PH/Redox Measurement in Chemical Processes. pH-Electrodes. Industrial Probes. Sensors," published by Ingold Messtechnik A G, CH-8902 Urdorf/Switzerland, 1990, p. 16.

Similarly to the above mentioned ion-selective sensors, this device comprises an integral, monolithic glass design which is only operational in a predefined spatial position and is not intended for harsh conditions.

Another known ion-selective sensor (the US' Foxboro Company booklet, "pH/ORP/ISE Sensors B71 pH Series," The Foxboro Company, Foxboro Mass. 02035-2099, 1993, p. 1) was designed for fluorine and hydrogen ion activity monitoring and is suitable for redox potential monitoring applications.

This sensor incorporates a plastic housing tube where a detachable indicator electrode is rigidly fixed in addition to a reference electrode that has a hollow body filled with liquid or gel electrolyte containing a solid dispersed material which forms a spatial structure that is freely movable inside the reference electrode. An indicator electrode filled with liquid electrolyte, together with a solid ion-selective sensor, are installed into the housing tube for ion activity monitoring, and an indicator electrode with a platinum sensing element is inserted into the housing tube for redox potential monitoring.

Compared to the previously mentioned sensors, the claimed device is more flexible in use and therefore has wider applications.

However, all above mentioned disadvantages apply to the latter sensor. They are attributed to the liquid or gel-type electrolyte present in the reference electrode and the liquid electrolyte inside the indicator electrode. This requires frequent refillings of the reference electrode electrolyte, poses spatial limitations for sensor operation and restricts harsh-environment applications.

DETAILED DESCRIPTION OF THE SPECIFIED EMBODIMENTS

The proposed invention is built around the design of a multipurpose ion-selective sensor in an embodiment that would eliminate electrolyte movements inside the electrodes and its entry into the analysed liquid thereby making it functional in any spatial position, critical operating environments, and under any ion composition and redox potential.

This challenge has been met by a multipurpose ion-selective sensor which incorporates a housing tube with a detachable indicator electrode that is fixed to, and is electrically connected with a measurement transmitter, whereby the electrode has an indicator system with a sensing membrane immersed into the analysed liquid; the reference electrode comprises a hollow body with electrolyte filled with a solid dispersed material forming a spatial structure in the electrolyte, a potential-forming semi-element and a connecting member which is contacting the analysed liquid. According to the proposed layout, both the indicator system and its sensing probe have a solid-state design; the reference electrode has an internal surface, and its spatial structure is rigidly linked with this surface and the connecting member.

In this way, the proposed ion-selective sensor employs electrodes which are essentially immune to gravity and enable any spatial position for normal operation. This design eliminates electrode damage at high temperatures (around 200° C.) high pressures (around 5 MPa), zero-gravity conditions and low temperatures of some −60° C., thereby ensuring full operability in extreme conditions. Moreover, the design eliminates the electrolyte entry from the reference electrode and thus greatly extends the useful service life of the claimed sensor. This sensor design enables its application for redox potential measurements in analysed liquids with no regard to sensor spatial position and operating environment.

One and two-chamber designs are available for the reference electrode. For the both embodiments, the electrolyte spatial structure in each chamber of the reference electrode is rigidly linked with internal walls of said chambers, the potential-forming member, each connection member and external wall of the internal chamber.

In the single-chamber reference electrode embodiment, the said rigid link of the spatial structure is achieved by a solid dispersed material of the reference electrode electrolyte, in quantity sufficient for 5–30 wt. % concentrations whereby the said material contains acrylamide and NN$^1$-methylemebisacrylamide monomers in proportions of 5–35 weight parts of acrylamide per one weight part of NN$^1$-methylemebisacrylamide as well as a monomer polymerisation initiator; in the two-chamber reference electrode embodiment, the second solid dispersed material is present in the internal electrolyte, in quantities suitable for 0.1–5 wt. % concentrations and with a similar composition to the solid dispersed material of the electrolyte contained in the reference electrode body.

This enables various designs of solid-electrolyte indicator electrodes to be mounted in the sensor housing tube where the said electrodes should be the most appropriate for individual analysed liquids and, most importantly, will enable the solid-state configuration of their indicator system and the sensing member.

For instance, the indicator electrode can be configured with a hollow glass body with its one end portion incorporating an indicator system comprising an envelope made of sensitive glass, and an internal surface where the solid electrolyte is connected with a measurement transmitter by an electric conductor. The said sensitive glass can be either a ion-selective grade or a glass sensitive to electron transfer into redox processes.

An indicator electrode can be installed for individual liquids under analysis where the electrode can be either selective to a specified ion of the analysed liquid or, optionally, be suitable for monitoring the redox potential.

For example, the indicator electrode can comprise an inert material body with its indicator system located at one end portion, the said system comprising a ion-selective membrane having an internal surface with a solid electrolyte thereon and connected to the measurement transmitter by an electric conductor; alternatively, an indicator electrode can be made with an inert material body and its indicator system provided in one end portion, with the said system comprising a noble-metal sensitive membrane connected to the measurement transmitter by an electric conductor.

The sealed sensor housing tube design and reliability improvements as well as easier sensor maintenance, assembly and disassembly for electrode replacement are achieved by means of the first sensor sealing member enabling the detachable fixing of electrodes within the housing tube; the first sealing member can accommodate at least one sealing element made of an elastic O-ring positioned on the external surface of a side wall of each electrode; the sensor housing tube can be made hollow with removable inert-material filler therein, fixed in the housing by the second sealing member; holes are made in the filler in the latter case which are essentially parallel to the housing tube's longitudinal axis, and the electrodes are rigidly fixed in these holes where each filler comprises a cylinder member with external surface fitting the internal surface of the sensor housing tube, while the second seal having at least one sealing element comprising an elastic O-ring securely positioned on the external surface of the filler side wall.

Low-volume monitoring of analysed liquids including laboratory measurements can be facilitated by an embodiment where the sensor housing tube can optionally comprise the first and the second coaxially fixed, detachable members which are isolated from each other; the reference electrode is rigidly positioned in the first portion of the housing tube and at least one indicator electrode is rigidly fixed in its second portion.

The sensor maintenance is facilitated by electrode connections with the measurement transmitter by means of current terminal wires connected at their one end by detachable contact sockets to wires of related electrodes and at the other end to a cable connector of the measurement transmitter.

For measurement accuracy improvements, the sensor can be fitted with a RTD which is electrically connected to the measurement transmitter, the RTD can be located outside the sensor in proximity of the electrode area or inside the sensor.

For convenience and operating simplicity, the sensor housing tube can be fitted with a holder for securing the sensor in the analysed liquid zone; special grooves should be made in the sensor housing tube in the holder fixing portion, said grooves should be provided with elastic O-rings and the holder should be connected with the housing by means of a threaded connection and be sealed by the mentioned elastic members. Besides, the sensor can be fitted with at least one intermediate member which is hermetically sealed between the sensor housing and the holder.

As such, the claimed design enables a multipurpose sensor to be made for monitoring ion activity of various chemical elements including hydrogen ions, and redox potential by means of the same device which is operable in any spatial position and extreme conditions; the said device eliminates reference electrode refillings with electrolyte thereby significantly extending the useful service life of the sensor and, as necessary, enables quick and easy replacements of electrodes secured in the sensor housing tube.

BRIEF DESCRIPTION OF THE DRAWINGS

For better understanding of the claimed fundamentals, individual application examples are hereinafter provided with references to attached drawings including:

THE BEST EMBODIMENT OF THE INVENTION

Figure 1:
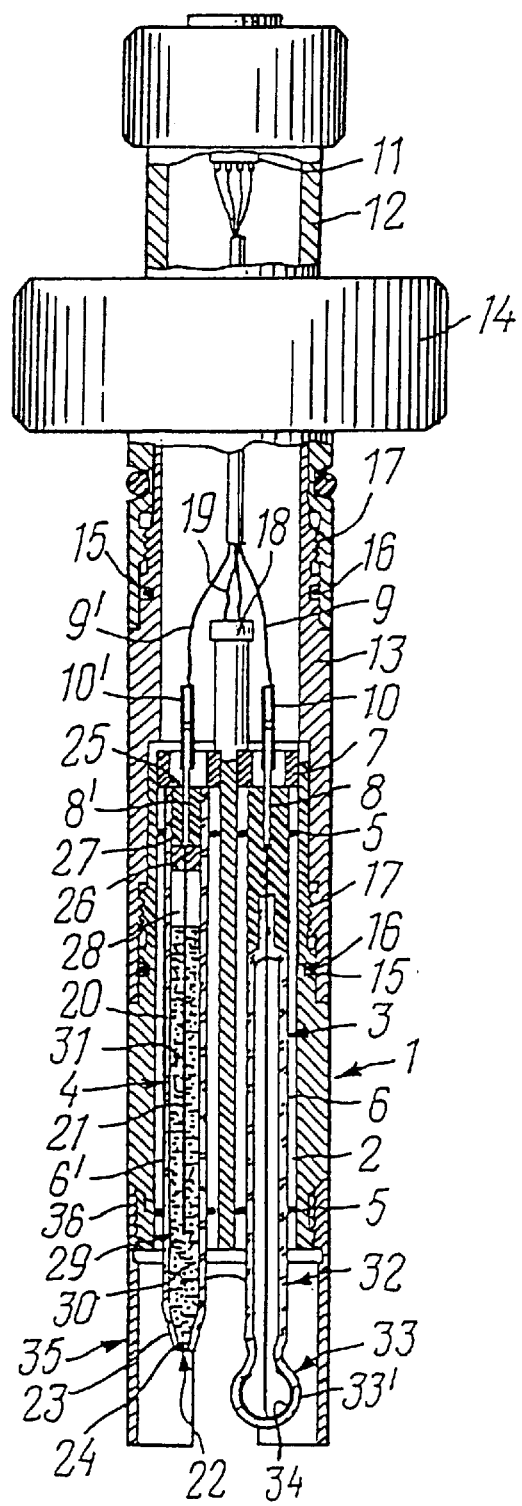
FIG. 1—A multipurpose ion-selective sensor made according to the present invention, a longitudinal section.

The multifunctional ion-selective sensor made according to the present invention incorporates the housing tube (FIG. 1) which comprises a metal cylinder that has two holes (2) made essentially parallel to the longitudinal axis of the said cylinder; the holes accommodate an indicator electrode (3) and a reference electrode (4). One, two and more holes can be optionally made in the housing tube for placing the indicator electrodes. The number of indicating electrodes depends on composition of analysed liquid, that is on availability of various ions with activities which can be simultaneously monitored by the proposed sensor.

Electrodes (3) and (4) have cross-sections which are smaller than those of related holes (2), to enable fast removal of electrodes (3) and (4) from the housing tube (1) when necessary. The electrodes (3, 4) are sealed in the housing (1) by sealing members made of elastic O-rings (5), such as rubber rings, and placed on the external side wall surface (6, $6^1$) of electrodes (3, 4). Each electrode is fixed in the housing tube (1) for protection from longitudinal motion by means of a restrictor (7) comprising a collar which is rigidly fixed (pressed) in the sensor housing tube (1).

Each electrode (3, 4) is electrically connected by a wire (8, $8^1$) to the measurement transmitter (not shown in the drawing). This electric connection comprises current terminal wires (9, $9^1$) connected at one end with detachable contact sockets (10, $10^1$) to conductors (8, $8^1$) of related electrodes (3, 4) and at another end to a socket (11) of the measurement transmitter cable connector.

The sensor has a hollow holder (12) for positioning it in the analysed liquid zone. A tubular intermediate member (13) is installed between the housing tube (1) and the holder (12) for extension of the housing (1), where the said member (13) is tightly fixed on the housing tube (1) and the holder (12), with the latter having a mounting nut (14). Annular grooves (15) are made on the external surfaces of the housing tube (1) and the intermediate member (13), the said grooves have elastic O-rings (16) and a thread connector (17). Depending on size of a process vessel for the analysed liquid and a sensor mounting location (not shown in the drawing), the sensor can optionally have two, three or more intermediate members (13) with different lengths, or no such members at all. In this way, the sensor housing tube (1), the holder (12) and the intermediate member (13) comprise an encapsulated, collapsible assembly which eliminates entry of the analysed liquid therein, whatever the external conditions exist.

The sensor is packaged with a RTD (18) for measurement of analysed liquid temperature, the RTD is positioned inside the said encapsulated, collapsible assembly which is contacting the internal surface of the sensor housing tube (1) and is connected to the measurement transmitter by electric conductors (19). Optionally, the RTD (18) can be mounted on external surface of the sensor (not shown in the drawing) in proximity of the electrode (3, 4) zone.

As described above, the electrodes (3, 4) are retractably mounted in the housing tube (1) and can be quickly replaced as required.

FIG. 1 illustrates the reference electrode (4) which comprises a hollow glass body (20) with a Ag/AgCl potential-forming semielement (21) connected by the electric wire (8), and a connecting member (22) is available for contact with the analysed liquid. In this configuration, the connecting member (22) comprises a hole made in the end portion (23) of the reference electrode (4) projected from the housing (1), with the said end portion incorporating a porous ceramic membrane (24). In another possible connecting member configuration, the membrane can be made of a porous glass or asbestos cord.

A rubber plug (26) and a cap (27) are rigidly mounted in the body (20) of the reference electrode (4) near its end (25), opposite the projecting end (23), for securing the electric conductor (8); they are isolating the body (20) space (28) of the reference electrode (4). The said space (28) is filled with electrolyte (29) containing a solid dispersed material which forms a spatial structure (30) in the electrolyte where this structure is rigidly linked with internal surface (31) of the reference electrode (4) body (20), the potential-forming semielement (21) and the connecting member (22). Optionally, the said electrolyte can be based on a saturated potassium chloride solution.

This solid dispersed electrolyte contains acrylamide and $NN^1$-methylemebisacrylamide monomers in the following proportion: from 5 to 35 weight parts of acrylamide per one weight part of $NN^1$-methylemebisacrylamide, in addition to any known monomer polymerisation initiator such as riboflavin.

The solid dispersed material is present in the electrolyte (29) in quantities sufficient for its concentrations from 5 to 30 wt. %.

Employment of the solid dispersed material with the proposed composition and concentration range in the electrolyte (29) will facilitate build-up of an elastic polymer spatial structure within the electrolyte (29) featuring rigid links with the internal surface (31), the potential-forming semi-element (21) and the connecting member (22). The electrolyte (29) comprises a rubber-type material that can withstand the environmental impacts in extreme conditions and maintain a fixed position within the interior (26) of the reference electrode (4) body (20) in any spatial arrangement of the sensor. The mentioned monomer ratio will secure strength of mechanical links with the described reference electrode (4) members within the spatial structure (30).

When more than 35:1 acrylamide is present in the system, the solid dispersed material is likely to fail forming the aforenamed spatial structure (30), but rather the long fibres with irregular interconnections.

If less than 5:1 acrylamide is present, this is likely to lead to a heterogeneous spatial structure in the electrolyte (29) with brittle mechanical properties and weak links with body walls (20) and with the connecting member (22).

When less than 5 wt. % of the solid dispersed material is present in the electrolyte (29), rigid connection of the spatial structure (30) with the connector member (22) can be affected by environmental impacts under extreme conditions.

If more than 30 wt. % of the solid dispersed material is present in the electrolyte (29), salt solubility would be lower and would hamper the measurement accuracy.

The indicator electrode (3) of the proposed sensor can employ any known indicator electrode design featuring a solid-state, ion-selective membrane with a solid electrolyte, or any known indicator electrode with a solid member which is sensitive to electron transfer into redox processes.

FIG. 1 highlights the indicator electrode (3) with a hollow glass body (32), whereby an indicator system (33) is positioned and is extending from the body (32) at one end portion, the said system includes a sensing member in the form of a spherical envelope ($33^1$) made of ion-selective glass, for example the grade selectively sensitive to hydrogen, sodium ions or those of any other element.

The said envelope ($33^1$) has internal surface on which a solid electrolyte (34) is positioned and is connected to the measurement transmitter by electric wire (8).

The similar design applies to an indicator electrode with a sensing member in the form of a glass envelope sensitive to electron transfer to redox processes.

In these embodiments of the indicator electrode, the sensor employs a device (35) for protection of the envelope ($33^1$) from mechanical damage, where the said device could comprise a slotted collar fixed on the housing tube (1) of the sensor by a threaded connector (36) in the envelope ($33^1$) zone.

The indicator electrode can have any other known embodiment that fits similar applications, but it is critical that the indicator system and sensing member be the solid-state design.

For instance, in one configuration, the indicator electrode (not shown in the drawing) can have a body made of inert material such as polyarylate, with an indicator system at its one end portion, where the sensing member of the said system comprises a solid ion-selective membrane with internal surface and a solid electrolyte thereon, connected to the measurement transmitter by electric wire, or alternatively the indicator electrode can comprise an inert material body such as glass, with its indicator system mounted at its one end portion, comprising a sensitive membrane made of a noble metal and connected to the measurement transmitter by electric wire.

Figure 2:
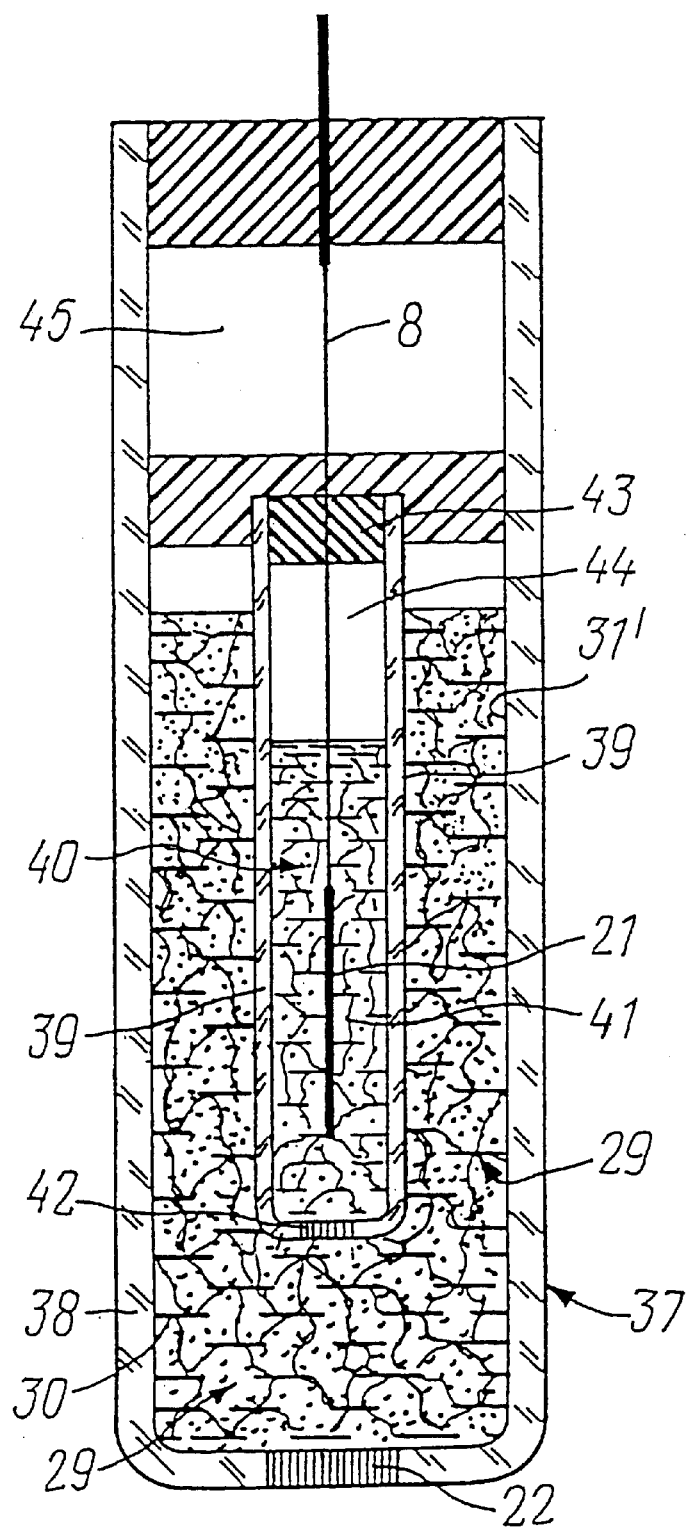
FIG. 2—The reference electrode made according to the present invention, a longitudinal section.

FIG. 2 illustrates another reference electrode (37) embodiment where a hollow glass body (38) has a fixed hollow glass envelope (39) incorporating a potential-forming semi-element (21) and internal electrolyte (40) with a solid dispersed material forming a spatial structure (41) in the said electrolyte (40). At one end portion, near a connecting member (22) of the body (38), the envelope (39) has a connecting member (42) for contact with electrolyte (29) within the reference electrode (37) of the body (38) where the said member can be made similar to a connecting member (22) of this body (38); there is a rubber or epoxy plug (43) for sealing the envelope (39) area (44) at the other end portion.

The spatial structure (41) is rigidly linked with the internal surface of the envelope (39), with the potential-forming semi-element (21) and the connecting member (42), while the external surface of the envelope (39) is rigidly linked with the spatial structure (30) of electrolyte (29) present in the interior (45) of the reference electrode (37) body (38), where the said interior (45) is also rigidly linked with internal surface ($31^1$) of its body (38) and its connecting member (22).

The solid dispersed material is present in the internal electrolyte (40) in quantity sufficient for 0.1–5 wt. % concentrations and has a similar composition to that of a solid dispersed material in electrolyte (29) present in the body (38) of the reference electrode (37). The above mentioned concentrations of the solid dispersed material are sufficient for building a spatial structure (41) which is rigidly linked with the said envelope (39) members. As soon as there is no contact between the internal electrolyte (40) and the analysed liquid, the former is immune to environmental impacts and thereby enables the appropriate concentrations of the solid dispersed material for required measurement accuracy.

No spatial structure (41) can be formed if the solid dispersed material concentration in the electrolyte (40) is lower than 0.1 wt. %, and measurement accuracy can be hampered when its concentration is above the 5 wt. % level.

Figure 3:
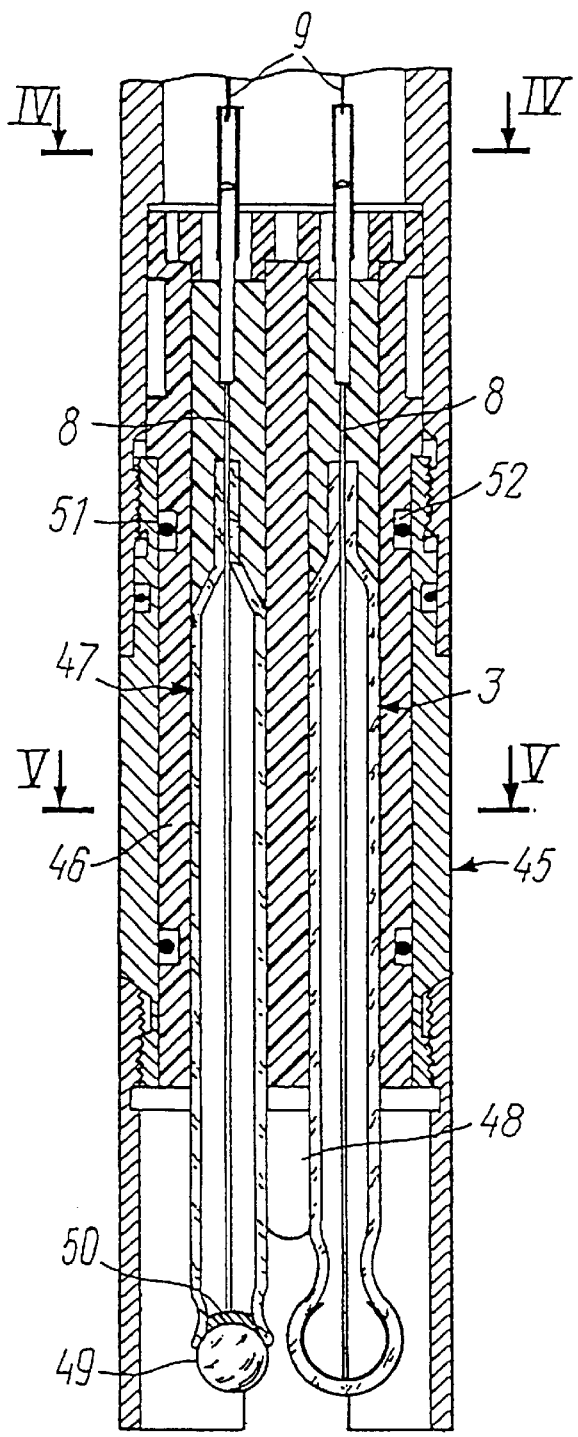
FIG. 3—The multipurpose ion-selective sensor fabricated in compliance with these claims; alternative embodiment, a longitudinal section with a torn-off segment.
Figure 4:
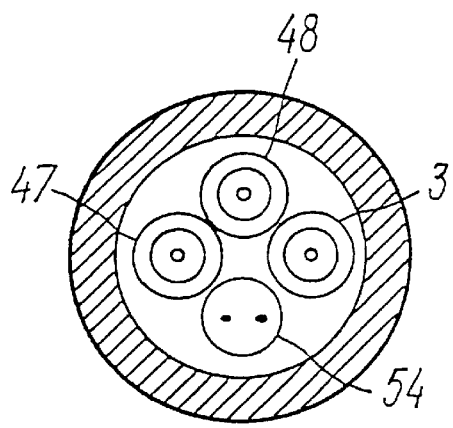
FIG. 4—Cross-section IV—IV in FIG. 3.
Figure 5:
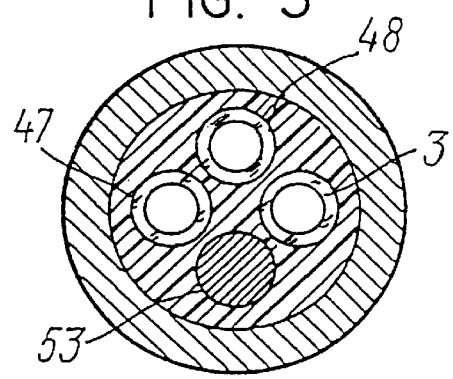
FIG. 5—Cross-section V—V in FIG. 3.

FIGS. 3 through 5 illustrate a sensor with a hollow metal housing tube (45) which accommodates an insert (46) made of inert material such as heat-resistant plastic. Through holes are made in the insert (46) essentially parallel to a longitudinal axis of the housing tube (45), to accommodate electrodes (47, 3, 48) rigidly fixed therein by means of filling a silicone hermetic glue or epoxy resin, as an example.

The sensor has one reference electrode (48) which is similar to that shown in FIG. 2, and two indicator electrodes (3) and (47). One indicator electrode (3) has a similar design to that shown in FIG. 1 and is intended for monitoring hydrogen ions, and another indicator electrode (47) features a spherical glass sensing member (49) which is sensitive to electron transfer to redox reactions; the latter has a solid electrolyte (50) thereon which is connected by electric wire (8) to the measurement transmitter.

The insert (46) comprises a cylindrical member with its outer surface matching the internal surface of the housing tube (45), wherein the said insert (46) is designed for easy removal from the housing (45). The insert (46) is fixed in the housing tube (45) by a sealing device containing O-rings (51) made of elastic material such as rubber and placed in annular grooves (52) made on the external side surface of the insert (46). The number of these grooves (52) and O-rings (51) depends on aggressiveness of the analysed liquid and extreme conditions expected for sensor operation.

Depending on operating conditions and measurement accuracy requirements, the reference electrode (48) of this sensor can be optionally a one-chamber (FIG. 1) or a two-chamber (FIG. 2) design.

The insert (46) has another opening which is essentially parallel to the electrode holes (3, 47, 48), the said opening accommodates a heat conductor (53) with its one end projecting from the housing tube (45) and contacting the analysed liquid and another end contacting the RTD device (54).

Figure 6:
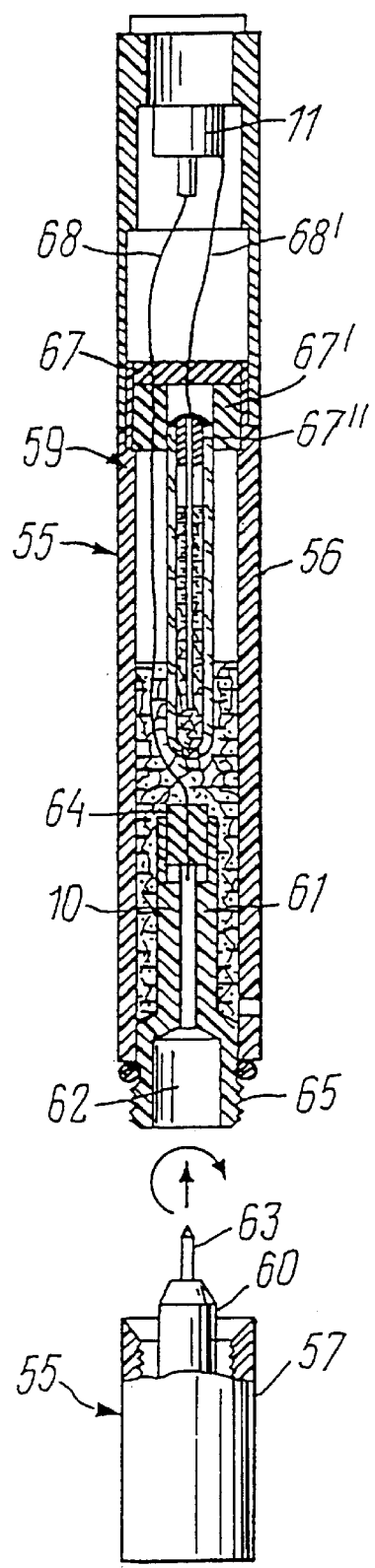
FIG. 6—Multipurpose ion-selective sensor made in accordance with the present invention; alternative embodiment, a longitudinal section.

FIG. 6 shows a sensor configuration with its housing tube (55) made of inert material such as polystyrene, and comprises two parts (56) and (57) which are coaxially fixed to each other and enable quick disconnection; they are isolated from each other by means of a connecting member (see FIG. 6). In the first portion (56) of the sensor housing tube (55) a reference electrode (59) is rigidly fixed, its two-chamber design is similar to the reference electrode (37) shown in FIG. 2, but the body of the former is made of inert material and comprises the first part (56) of the sensor housing tube (55); the connecting member (22) is contacting the analysed liquid and is positioned on the side surface of the housing (55) first part (56), in proximity of its connection with the second part (57). The second part (57) of the sensor housing tube (55) accommodates a rigidly fixed indicator electrode (60) which can be optionally made similar to the above mentioned one, when its body is made of inert material. In one modification, two, three or more indicator electrodes (60) can be rigidly fixed in this part (57) of the housing (55).

The connection member between two parts (56) and (57) of the sensor housing tube (55) is fitted with a shaped collar (61) made of inert material such as plastic, pressed in the first part (56) and effectively isolating its interior. A recess (62) is made in the collar (61) for accommodation of an indicator electrode (60) portion with its associated electric wire (63) as well as a through hole for a contact socket (10) and a plug (64) for isolation of the recess (62) and opening from electrolyte in the body (56) of the reference electrode (59). In its portion projecting from the first portion (56) of the housing tube (55), the collar (61) of the connecting member (59) has external thread (65) and a sealing member comprising optionally a rubber O-ring, while the second part (57) of the housing (55) is rigidly fixed thereon by means of the said thread (65) and is sealed relatively to the first part (56) by a rubber O-ring. The electric conductor wire (63) of the indicator electrode (60) is connected to the contact socket (10) switched to the measurement transmitter cable. The reference electrode (59) has a rubber and a plastic O-rings (67, 67[1] and 67[11]) through which the current terminal wires (68) and (68[1]) of the indicator electrode (60) and reference electrode (59) are passed for connection of electric wires (63) and (8) of electrodes (60) and (59) with a measurement transmitter cable socket (11).

Table 1 hereinafter presents five examples of reference electrode electrolyte compositions.

TABLE 1

| No. | Sensor design drawing, according to the present invention | Total monomer concentration, wt. % in reference electrode body electrolyte | in internal electrolyte | A*:M** monomer ratio in reference electrode body electrolyte | in internal electrolyte | Salt concentration, mole/liter in reference electrode body electrolyte | in internal electrolyte | Details |
|---|---|---|---|---|---|---|---|---|
| 1 | FIG. 1 | 5 | — | 35:1 | — | 3M KCl | — | Ratings: temperature range of −60° C. to 200° C.; 1.6 MPa pressure |
| 2 | FIG. 1 | 18 | — | 20:1 | — | 3M KCl | — | Same |
| 3 | FIGS. 3 through 5 | 30 | 5 | 35:1 | 5:1 | 1M KCl | 3M KCl | Same |

TABLE 1-continued

| No. | Sensor design drawing, according to the present invention | Total monomer concentration, wt. % in reference electrode body electrolyte | in internal electrolyte | A*:M** monomer ratio in reference electrode body electrolyte | in internal electrolyte | Salt concentration, mole/liter in reference electrode body electrolyte | in internal electrolyte | Details |
|---|---|---|---|---|---|---|---|---|
| 4 | FIG. 6 | 10 | 0.1 | 20:1 | 10:1 | 2M KCl | 1M KNO$_3$ | Ratings: temperature range of −60° C. to 80° C.; 1.6 MPa pressure |
| 5 | FIG. 6 | 10 | 2.5 | 10:1 | 10:1 | 0.1M KCl | 5M KNO$_3$ | Same |

* Acrylamide.
** NN$^1$-methylenebisacrylamide.

It can be seen from the five examples above that each sensor produced in accordance with the present invention is operable at extreme conditions.

The multipurpose ion-selective sensor has the following operating principle:

The proposed sensor is immersed into the analysed liquid in its portion where the indicator system (33), a sensing member of the indicator electrode (3, 47, 60) and a connecting member of the reference electrode (4, 37, 48 and 59) are mounted. The resultant solid-state indicator electrode (3, 47 and 60) potential is proportional to activity logarithm of the analysed ion. The reference electrode (4, 37, 48 and 59) generates the potential which is not dependent on analysed liquid composition. Transfer of salt ions from the reference electrode (4, 37, 48 and 59) electrolyte (29, 40) that is saturated by this salt closes the electric circuit through the analysed liquid whereby the potential drop is directly proportional to an analysed ion activity logarithm. When it is necessary to change the function of the indicator electrode (32, 47, 60), the existing indicator electrode is replaced by another one; this enables measurements of a different parameter, for instance, ion activity of hydrogen or any other chemical. In case of failure of any sensor electrode (3,47, 60,4,37,48 or 59), sensor operation can be resumed after easy and simple replacement of a faulty electrode by a new one.

In another embodiment (Example 6), the multipurpose ion-selective sensor can be manufactured complete with an interchangeable solid-electrolyte indicator electrode and a reference electrode shown in FIG. 1. A solid-electrolyte glass electrode is used as an indicator electrode shown in FIG. 1; the said electrode under-goes thermal water and steam sterilisation. The indicator system of the pH-metering indicator electrode comprises a 9 mm diameter sphere welded into a glass tube with 6 mm external diameter. The total length of the indicator electrode, including a pin plug, is 92 mm. The reference electrode comprises a glass body with 5 mm diameter and 82 mm length (together with a pin plug). The lower end portion of the reference electrode has a welded connecting member made of a porous ceramic material. The Ag/AgCl potential-forming semi-element is immersed into a thermally resistant electrolyte based on saturated solution of potassium chloride and a solid dispersed polymer containing acrylamide and NN$^1$-methylenebisacrylamide with 30 wt. % total concentration and 10:1 ratio. A pin plug terminal made in the glass body is sealed by a permanent-action glue.

The sensor made according to the present invention is installed in a fermenter with a 100 liter volume by means of a 25 mm dia. weld-in socket in a fermenter bottom in a reversed position and is fixed by a captive nut. Another socket with a 15° canting angle is used for an immersion sensor, InFit 764, fitted with a combined sterilised pH electrode, 465-5-S7 (both the electrode and the sensor are from Switzerland's Ingold). A similar Ingold sensor is installed in a horizontal weld-in socket.

Three above mentioned sensors should be sterilised in a nutrient medium directly in the fermenter, followed by growing of Pen. Chrisogenum. A complex nutrient medium is used. Automated pH monitoring uses all above mentioned sensors connected to related measurement transmitters. Cultural medium samples are regularly taken from the fermenter for pH measurements by a bench pH-meter. The analytical laboratory results are then compared with Ingold sensor readings and those produced by the claimed sensor.

The Ingold sensor is installed horizontally and cannot provide the fermenter process pH measurements a soon as the indicator electrode electrolyte cannot provide, in this position, an electrical contact between the internal surface of its indicator system and the potential-forming semi-element, and the electrolyte contact is lost in the reference electrode between the potential-forming semi-element and the connecting member. Both the claimed sensor and that installed with a 15° canting angle provide readings which closely correlate with the laboratory electrode indications.

Test results are summarised in Table 2.

TABLE 2

| | | pH readings | | | Differential pH readings | | |
|---|---|---|---|---|---|---|---|
| | Time, h | claimed sensor | 465 model sensor | SK2403S bench device | (4)–(5) | (3)–(5) | (3)–(4) |
| No. 1 | 2 | 3 | 4 | 5 | 6 | 7 | 8 |
| 1 | 0 | 6.22 | 6.17 | 6.20 | −0.03 | 0.02 | 0.05 |
| 2 | 24 | 6.32 | 6.33 | 6.32 | 0.01 | 0.00 | 0.01 |
| 3 | 48 | 6.84 | 6.89 | 6.84 | 0.05 | 0.00 | −0.05 |
| 4 | 72 | 6.86 | 6.87 | 6.86 | 0.01 | 0.00 | −0.01 |
| 5 | 96 | 6.24 | 6.24 | 6.28 | −0.04 | −0.04 | 0.00 |
| 6 | 120 | 6.31 | 6.35 | 6.34 | 0.01 | −0.03 | −0.04 |

It can be seen from the examples above that the pH measurements produced during a long fermentation process by the claimed sensor installed in a reversed position have been found to be in good agreement with readings of a commercial Ingold sensor installed at a 15° canting angle and the RADIOMETER laboratory electrode. The maximum deviation of readings is within 0.05 pH. However, the Ingold sensor appears inoperable when installed horizontally.

Measurement accuracy evaluation for the claimed sensor is performed following multiple sterilisations and a mounting scheme, together with the Ingold's sensor, which is similar to the pH monitoring experiments described above. The claimed sensor is mounted in the fermenter in a reversed position while the Ingold's one at the 15° canting angle. The fermenter is sterilised under 132° C. temperature during one hour. The consecutive sterilisation procedures are repeated five times with the sensors being immersed into the fermenter and with no adjustments made to readings of each sensor after a sterilisation cycle. The fermenter is sampled periodically for pH measurements using a RADIOMETER laboratory meter. Test results are summarised in Table 3.

TABLE 3

| | | pH readings, | | | | |
|---|---|---|---|---|---|---|
| | | | | | Differential pH readings | |
| | Sterili- | claimed | 465 model | SK2403S | | |
| No. | sations | sensor | sensor | bench device | (4)–(5) | (3)–(5) | (3)–(4) |
| 1 | 2 | 3 | 4 | 5 | 6 | 7 | 8 |
| 1 | 1 | 7.80 | 7.95 | 7.70 | 0.25 | 0.10 | −0.15 |
| 2 | 2 | 6.68 | 6.92 | 6.78 | 0.14 | −0.07 | −0.24 |
| 3 | 3 | 7.04 | 7.33 | 6.96 | −0.37 | −0.08 | −0.29 |
| 4 | 4 | 7.01 | 7.43 | 7.01 | 0.42 | 0.00 | −0.42 |
| 5 | 5 | 6.79 | 7.24 | 6.69 | 0.56 | 0.10 | −0.55 |

It can be seen from these examples that the claimed sensor maintains its calibration performance after multiple sterilisations and provides a good readings correlation with results obtained by the RADIOMETER laboratory electrode. The Ingold's pH readings are commonly deviating following each sterilisation cycle, thus leading to errors in excess of 0.5 pH when its readings are not adjusted. Therefore, the claimed sensor has been reported to have more consistent readings after multiple sterilisations; it maintains operability in any spatial position an is free from reinstallations while additional adjustments using buffer solutions, thus yielding significant maintenance advantages.

Replacement indicator and reference electrodes offer simple replacements during functional changes such as its customisation for activity measurements on individual ions or redox potential, or in case of electrode (indicator or reference) failures. Solid electrolytes in the indicator electrodes and the specified electrolyte for reference electrodes will maintain normal electrode operation in any position, under elevated temperatures and pressures as well as at temperatures below −0° C. and zero-gravity conditions.

Industrial Applications

The following industrial applications are possible for the present invention: biotechnology, for monitoring pH and redox potential in fermenters; chemical and pharmaceutical industries, pH and redox potential monitoring for chemical synthesis of derivatives used for production of antibiotic recipes such as Chloramphenicol and other synthetic preparations; heat and power engineering, for water treatment unit monitoring at thermal power plants; geology and environmental monitoring, for continuous, high-depth pH, redox potential and groundwater composition measurements.

The invention claimed is:

1. A multipurpose ion-selective sensor comprising:
   a hollow housing tube comprising a first connecting member and a second connecting member, fixed in an alignment, said connecting members being separable from each other;
   an indicator electrode electrically connected with a measurement transmitter, whereby the indicator electrode has a solid indicator system comprising a solid sensing membrane to be immersed into the analyzed liquid;
   a reference electrode comprising a first hollow body and a second hollow body wherein the first hollow body is located in the second hollow body;
   the first hollow body containing:
      a potential-forming semi-element located in the first hollow body, the semi-element is adapted to be electrically connected to the measurement transmitter,
      a first connecting element located in a surface of the first hollow body; and
      a first electrolyte filled with a first solid dispersed material forming a first spatial structure in the first electrolyte, located in the first hollow body, wherein the first spatial structure is rigidly linked with an internal surface of the first hollow body, the potential-forming semi-element and the first connecting element;
   the second hollow body containing:
      a second connecting element located in a surface of the second hollow body, for contacting an analyzed liquid; and
      a second electrolyte filled with a second solid dispersed material which forms a second spatial structure, located in the first hollow body, wherein the second spatial structure is rigidly linked with an internal surface of the second hollow body, an external surface of the first hollow body and the second connecting element;
   wherein the concentration of the first solid dispersed material in the first electrolyte is lower than the concentration of the second solid dispersed material in the second electrolyte; and
   wherein the reference electrode is rigidly fixed on the first connecting member and at least one indicator electrode is rigidly fixed on the second connecting member.

2. The multipurpose ion-selective sensor as set forth in claim 1, wherein the first solid dispersed material of the first electrolyte is present in the in the in the first hollow body in the quantity sufficient for its concentration to be between 0.1 and 5 wt. % and the second solid dispersed material of the second electrolyte is present in the second hollow body in the quantity sufficient for its concentration to be between 5 and 30 wt. %, whereby both solid dispersed materials contain acrylamide monomers and NN'-methylenebisacrylamide in proportion of 5 to 35 weight parts of acrylamide per one weight part of NN'-methylenebisacrylamide and a monomer polymerization initiator.

3. The multipurpose ion-selective sensor as set forth in claim 1, comprising a resistance temperature detector, which is electrically connected to the measurement transmitter.

4. The multipurpose ion-selective sensor as set forth in claim 3, wherein the resistance temperature detector is located outside the sensor in proximity of the electrode location.

5. The multipurpose ion selective sensor as set forth in claim 3, wherein the resistance temperature detector is mounted inside the sensor.

6. The multipurpose ion-selective sensor as set forth in claim 1, comprising the hollow housing tube with a holder for fixing it to a container containing the analyzed liquid zone.

7. A multipurpose ion-selective sensor comprising:
   a hollow housing tube;
   an indicator electrode located in the hollow housing tube, the indicator electrode is adapted to be electrically connected to a measurement transmitter; and
   a reference electrode comprising:
      a second hollow body;
      a first hollow body located in the second hollow body;
      the first hollow body containing:
         a potential-forming semi-element located in the first hollow body, the semi-element is adapted to be electrically connected to the measurement transmitter,
         a first connecting element located in a surface of the first hollow body; and
         a first electrolyte filled with a first solid dispersed material forming a first spatial structure in the first electrolyte, located in the first hollow body, wherein the first spatial structure is rigidly linked with an internal surface of the first hollow body, the potential-forming semi-element and the first connecting element;
      the second hollow body containing:
         a second connecting element located in a surface of the second hollow body, for contacting an analyzed liquid; and
         a second electrolyte filled with a second solid dispersed material which forms a second spatial structure, located in the first hollow body, wherein the second spatial structure is rigidly linked with an internal surface of the second hollow body, an external surface of the first hollow body and the second connecting element; and
   wherein the concentration of the first solid dispersed material in the first electrolyte is lower than the concentration of the second solid dispersed material in the second electrolyte.

8. The multipurpose ion-selective sensor of claim 7, wherein:
   the concentration first solid dispersed material in the first electrolyte is between 0.1 and 5 wt. %; and
   the concentration of the second solid dispersed material in the second electrolyte is between 5 and 30 wt. %.

9. The multipurpose ion-selective sensor of claim 8, wherein:
   the reference electrode and the indicator electrode are detachable from the hollow housing tube; and
   the indicator electrode comprises a solid sensing membrane to be immersed into the analyzed liquid, a solid electrolyte on an interior surface of the solid sensing membrane and a conductor in contact with the solid electrolyte and the measurement transmitter.

* * * * *